(12) United States Patent
Jackson et al.

(10) Patent No.: US 7,613,512 B2
(45) Date of Patent: Nov. 3, 2009

(54) GRADUALLY SYNCHRONIZED SIMULTANEOUS ATRIAL AND VENTRICULAR PACING FOR CARDIAC RHYTHM DISCRIMINATION

(75) Inventors: Troy E. Jackson, New Brighton, MN (US); Mark L. Brown, North Oaks, MN (US); Jeffrey M. Gillberg, Coon Rapids, MN (US)

(73) Assignee: Medtronic, Inc., Minneapolis, MN (US)

( * ) Notice: Subject to any disclaimer, the term of this patent is extended or adjusted under 35 U.S.C. 154(b) by 321 days.

(21) Appl. No.: 11/615,490

(22) Filed: Dec. 22, 2006

(65) Prior Publication Data

US 2008/0154322 A1 Jun. 26, 2008

(51) Int. Cl.
*A61N 1/36* (2006.01)
*A61N 1/368* (2006.01)
(52) U.S. Cl. .................................................. 607/14
(58) Field of Classification Search ............... 607/9, 607/14
See application file for complete search history.

(56) References Cited

U.S. PATENT DOCUMENTS

| 5,496,350 | A | 3/1996 | Lu |
| 5,702,424 | A | 12/1997 | Legay et al. |
| 6,330,477 | B1 | 12/2001 | Casavant |
| 6,658,292 | B2 * | 12/2003 | Kroll et al. ............... 607/19 |
| 2003/0088288 | A1 * | 5/2003 | Armstrong et al. .......... 607/14 |
| 2004/0172067 | A1 | 9/2004 | Saba |

* cited by examiner

*Primary Examiner*—George R Evanisko
*Assistant Examiner*—Andrew Hayes
(74) *Attorney, Agent, or Firm*—Michael C. Soldner

(57) ABSTRACT

A cardiac medical device used for delivering anti-tachycardia pacing in both the atrial and ventricular regions in a simultaneous manner, while preventing potential of inducing atrial arrhythmia. The pacing pulses may be synchronized in a gradual manner so that simultaneous delivery of the pulses is ultimately achieved at reduced risk of inducing atria arrhythmia. The pacing pulses may also be synchronized immediately after a determination is made whether simultaneous pacing purses will be delivered in the vulnerable regions of the cardiac cycle.

20 Claims, 9 Drawing Sheets

GRADUALLY SYNCHRONIZED SIMULTANEOUS ATRIAL AND VENTRICULAR PACING FOR CARDIAC RHYTHM DISCRIMINATION

BACKGROUND

The present invention relates generally to cardiac medical devices. In some embodiments, the invention relates generally to cardiac medical devices used both for monitoring the state of a patient and delivering therapy to the patient.

Cardiac medical devices can include diagnostic monitoring equipment, external medical device systems, and implantable medical devices (IMDs). Examples of such IMDs can include implantable hemodynamic monitors (IHMs), implantable cardioverter-defibrillators (ICDs), cardiac pacemakers, cardiac resynchronization therapy (CRT) pacing devices, and drug delivery devices.

As is known, ICDs are configured with one or more sensors, with each sensor generally used to monitor a distinct cardiac parameter of the patient. Upon interpreting one or more of the cardiac parameters as arrhythmic in nature, the ICDs, in turn, can be used to deliver an appropriate therapy to the patient, with such therapies including pacing and/or defibrillation. Unfortunately, identifying the exact source of an arrhythmia can sometimes be a challenge to both ICDs and the physicians taking care of patients with such ICDs.

For example, ICDs can have difficulty distinguishing between ventricular tachyarrhythmias and supraventricular tachycardias. As is known, ventricular tachyarrhythmias originate in the ventricular region of the heart, while supraventricular tachycardias originate above the ventricular region of the heart, e.g., in the atrial region of the heart or the atrioventricular (AV) node. As should be appreciated, ventricular tachyarrhythmias are considered the more severe cardiac event of the two for the patient.

One reason for the above-described difficulty is that measured signal parameters, for example, an electrogram (EGM) or timing of EGM from different chambers of the heart, for each of these cardiac events can be similar, and in turn, interpreted similarly by the ICDs. Because of this, in cases when supraventricular tachycardias occur, the ICDs may deliver inappropriate therapy. Such inappropriate therapies constitute a significant source of physical and emotional distress for patients, and can lead to early depletion of the ICD battery.

One specific example of a situation in which it can be difficult for the device to distinguish between ventricular tachyarrhythmias supraventricular tachycardias occurs when discriminating between supraventricular tachycardias having 1:1 antegrade conduction and ventricular tachyarrhythmias having 1:1 retrograde conduction.

In an attempt to solve the problem, those skilled in the art have used various mathematical algorithms to more effectively utilize the quantitative aspects of the signal parameters measured by the devices (e.g., EGM morphology, timing relationships between 2 or more EGMs, etc). This approach has generally been found to have variable success. By implementing these algorithms (e.g., via controllers) within ICDs, the incidence of inappropriate therapy was reduced from that of the early generation ICDs and the later developed dual-chamber ICDs. However, the inappropriate therapy was still found to occur.

What is needed are medical devices and systematic methods used to prevent the incidence of inappropriate therapy, while also being adapted to limit other risks to the patient when using such devices and methods.

DESCRIPTION OF THE DRAWINGS

Aspects and features of the present invention will be appreciated as the same becomes better understood by reference to the following detailed description of the embodiments of the invention when considered in connection with the accompanying drawings, wherein.

DETAILED DESCRIPTION

Figure 1:
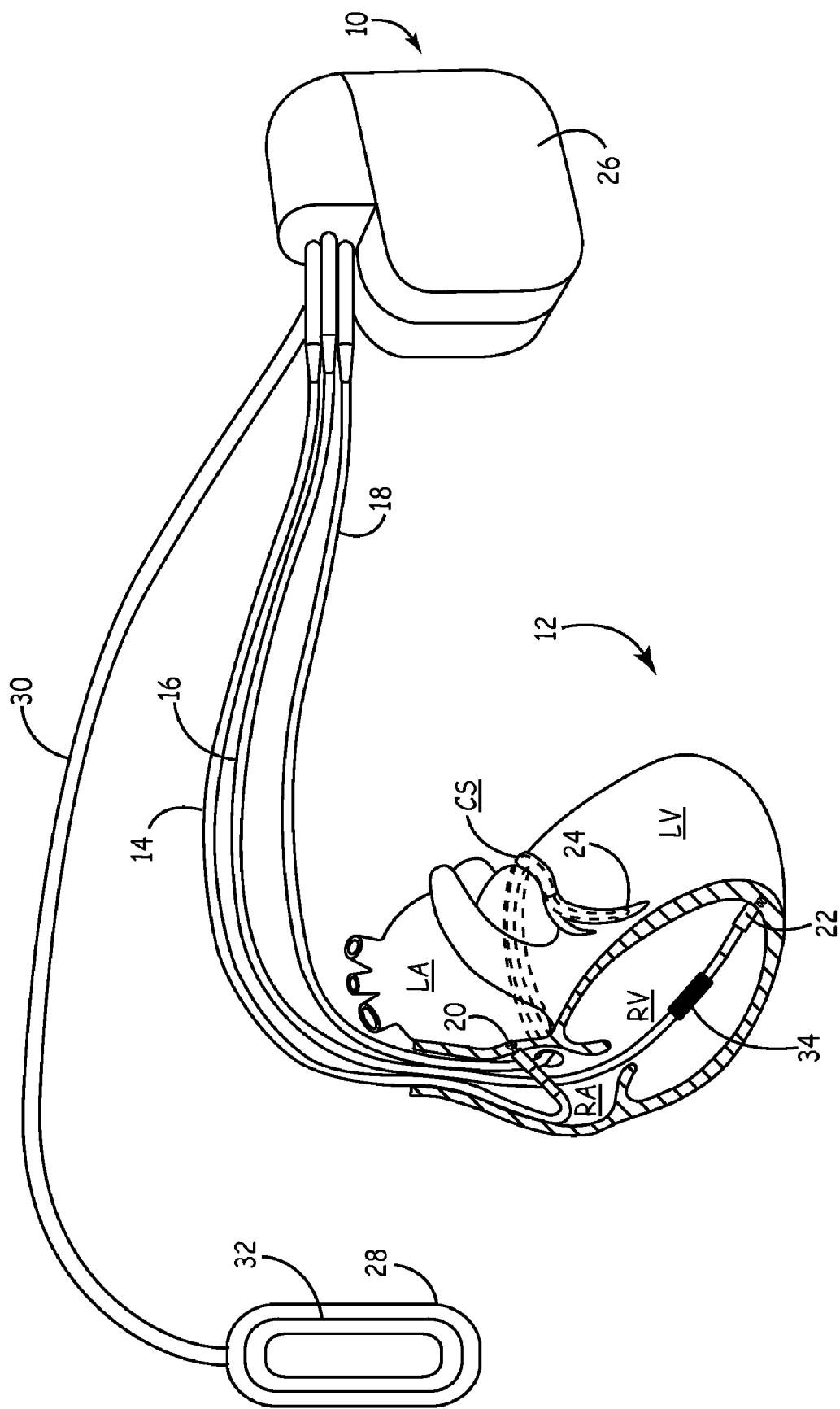
FIG. 1 is a schematic representation of an exemplary medical device that can be used in accordance with certain embodiments of the invention.

The following detailed description should be read with reference to the drawings, in which like elements in different drawings are numbered identically. The drawings depict selected embodiments and are not intended to limit the scope of the invention. It will be understood that embodiments shown in the drawings and described below are merely for illustrative purposes, and are not intended to limit the scope of the invention as defined in the claims. In addition, it should be appreciated that the techniques and methods described and illustrated herein can be implemented within a medical device in a variety of manners. For example, in certain embodiments, instructions corresponding to one or more of the techniques and methods are programmed within a controller (e.g., a processor) within such medical device. One skilled in the art would be familiar with such programming practices as well as other typical manners of implementation within medical devices. In turn, such manners of implementation are not discussed in further detail herein.

As described above, some methods used to address the incidence of inappropriate therapy from ICDs have involved using mathematical algorithms to more effectively utilize the quantitative aspects of the patient parameters. However, as mentioned above, even when using such methods, the inappropriate therapy was found to still occur.

Another more recent technique to limit the incidence of inappropriate therapy from ICDs involves the teachings of Saba, described in U.S. patent application Ser. No. 10/717,248 (the '248 patent application; U.S. Publication No. 2004/0172067), herein incorporated by reference in relevant part.

A limitation discovered with the technique described in the '248 application involves additional arrhythmic risk. While the simultaneous pacing technique can be used with ICDs to more effectively differentiate between arrhythmias in the ventricular and supraventricular regions of the heart in comparison to other methods, it has been found, at times, to also create conditions that are atrial proarrhythmic. As a result, atrial tachyarrhythmia, e.g., atrial fibrillation or atrial flutter, can be induced. The technique of the '248 application generally involves overdrive pacing of both the atria and ventricular regions in a simultaneous manner following sensing of an arrhythmic event (e.g., tachycardia). Following a triggering of the simultaneous pacing, there is potential for the corresponding pacing pulses delivered in the atria region to fall within the atria's vulnerable region of the cardiac cycle so as to induce atrial tachyarrhythmia.

The present invention includes the use of atrial and ventricular paced pulses that are synchronized so as to be delivered in a simultaneous manner. However, in certain embodiments, such synchronization is provided in a gradual manner so that simultaneous delivery of the pulses is ultimately achieved, yet with reduced potential of inducing atrial arrhythmia. As illustrated below, upon sensing actual or suspected tachycardia in both the atrial and ventricular regions, anti-tachycardia pacing is delivered to both regions. In certain embodiments, the atrial and ventricular pacing pulses are initially delivered out of phase with each other, with the atrial and ventricular pacing pulses each being delivered at cycle lengths to sufficiently overdrive the corresponding regions of the heart. As should be appreciated, the atrial pacing pulses are initially delivered and the atrial pacing cycle lengths are set so as to avoid delivery of pulses during the atrium's vulnerable region.

In certain embodiments, such atrial and ventricular pacing pulses are also delivered according to distinct cycle lengths. By having distinct cycle lengths for each of the pacing pulses, the pacing pulses delivered in one of the atrial or ventricular regions can be gradually brought into phase with the pacing pulses delivered in the other of the atrial or ventricular regions. In turn, such gradual shift of one of the pacing pulses with respect to the other pacing pulses enables one to continue to avoid delivery of atrium pacing pulses during the atria's vulnerable regions, and ultimately results in simultaneous delivery of the pulses. It should be appreciated that the embodiments of the invention could be applicable to any protocol in which one seeks to ultimately deliver a plurality of pacing pulses simultaneously.

FIG. 1 shows a schematic representation of an exemplary cardiac medical device 10 that can be used in accordance with certain embodiments of the invention. As shown, the cardiac medical device 10 is an IMD and in certain embodiments, an ICD; however, the invention should not be limited to any particular IMD or any cardiac medical device. Instead, any cardiac medical device could be utilized in embodiments of the invention so long as such device utilizes a plurality of electrodes or other sensors for monitoring the cardiac condition of a patient and for delivering therapy to the patient when necessary. In certain embodiments, such electrodes or other sensors are capable of measuring cardiac parameters or signals in supraventricular and ventricular regions, such as a patient's electrogram (EGM).

In FIG. 1, heart 12 includes the right atrium (RA), left atrium (LA), right ventricle (RV), left ventricle (LV), and the coronary sinus (CS) extending from the opening in the right atrium laterally around the atria to form the great vein.

FIG. 1 depicts the medical device 10 in relation to the heart 12. In certain embodiments, the medical device 10 can be an implantable, multi-channel ICD. As shown, three endocardial leads 14, 16, and 18 connect the medical device 10 with the RA, the RV and the LV, respectively. Each lead includes at least one electrical conductor and pace/sense electrode. For example, leads 14, 16 and 18 are respectively connected to pace/sense electrodes 20, 22, and 24. In addition, a can electrode 26 can be formed as part of the outer surface of the housing of the medical device 10. The pace/sense electrodes 20, 22, and 24 and can electrode 26 can be selectively employed to provide a number of unipolar and bipolar pace/sense electrode combinations for pacing and sensing functions. The depicted positions in or about the right and left heart chambers are merely exemplary. Moreover, other leads and pace/sense electrodes can be used instead of, or in combination with, any one or more of the depicted leads and electrodes.

Typically, in pacing systems of the type illustrated in FIG. 1, the electrodes designated herein as "pace/sense" electrodes are used for both pacing and sensing functions. In certain embodiments, these electrodes can be used exclusively as pace or sense electrodes or used in common as pace/sense electrodes in programmed combinations for sensing cardiac signals and delivering pace pulses.

In certain embodiments, a subcutaneous electrode 28 coupled to medical electrical lead 30 can be added to or substituted for one or more of the leads/electrodes depicted in FIG. 1. If electrode 28 is used, a suitable defibrillation coil 32 can be coupled to high voltage circuitry to deliver a defibrillation pulse. Also, while a coil electrode 34 is shown as being coupled to a portion of RV lead 16, such an electrode can be further coupled to portions of any of the leads of FIG. 1, such as LV lead 18. The coil electrode 34, the subcutaneous electrode 28, or other similar electrode types can be electrically coupled to low voltage circuitry in addition to high voltage circuitry. As is known, such electrodes can be disposed in a variety of locations in, around, and on the heart.

In addition, some or all of the leads 14, 16, and 20 shown in FIG. 1 could carry one or more pressure sensors for monitoring systolic and diastolic pressures, and/or a series of spaced apart impedance sensing leads for developing volumetric measurements of the expansion and contraction of the RA, LA, RV and LV. As described above, such pressure sensors and/or impedance sensing leads include examples of the many other sensors that could also be used for monitoring purposes (as opposed to or in combination with the pace/sense electrodes illustrated in FIG. 1) in embodiments of the invention. Further examples of the other sensors can include accelerometers, flow probes, microphones, sonometric crystals, metabolic or chemical sensors, and any electrical and/or mechanical sensors.

The leads and circuitry described above can be employed to record a plurality of cardiac parameters, e.g., EGM signals, blood pressure signals, and impedance values, over certain time intervals. The recorded data can be periodically telemetered out to a programmer operated by a physician or other healthcare worker in an uplink telemetry transmission during a telemetry session, for example.

Figure 2:
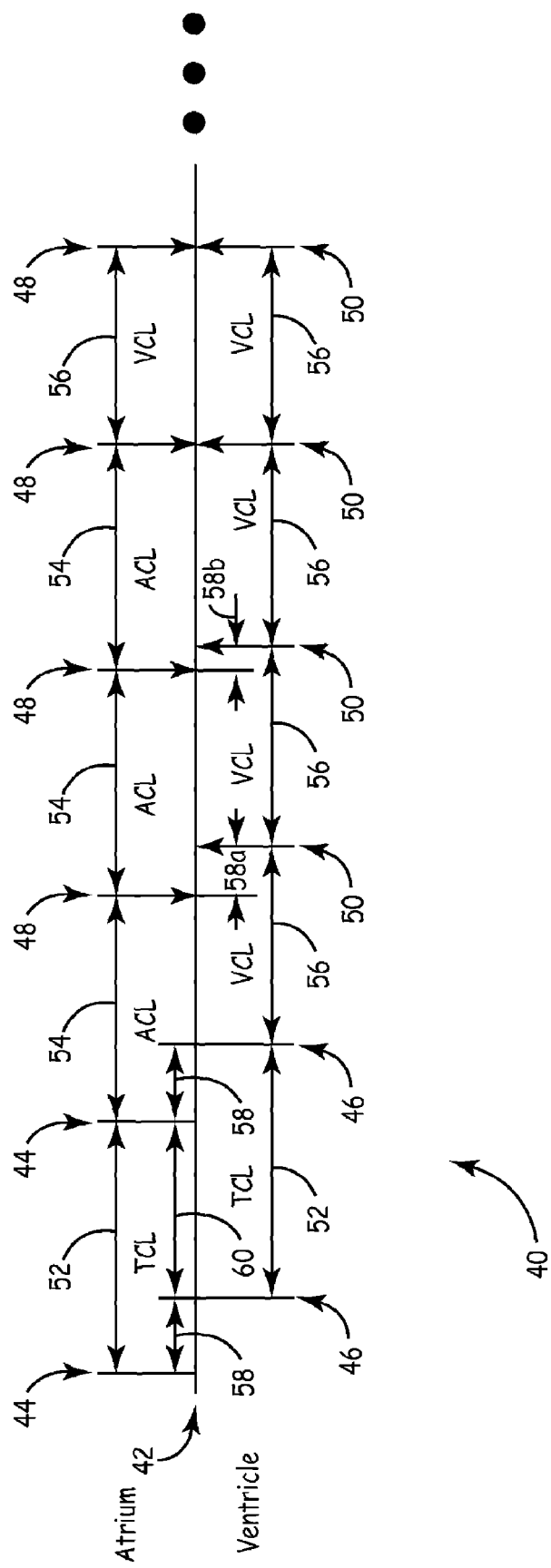
FIG. 2 is an exemplary timing diagram illustrating a technique used by the medical device of FIG. 1 for initially delivering anti-tachycardia pacing in the atrial and ventricular regions in accordance with certain embodiments of the invention.
Figure 3:
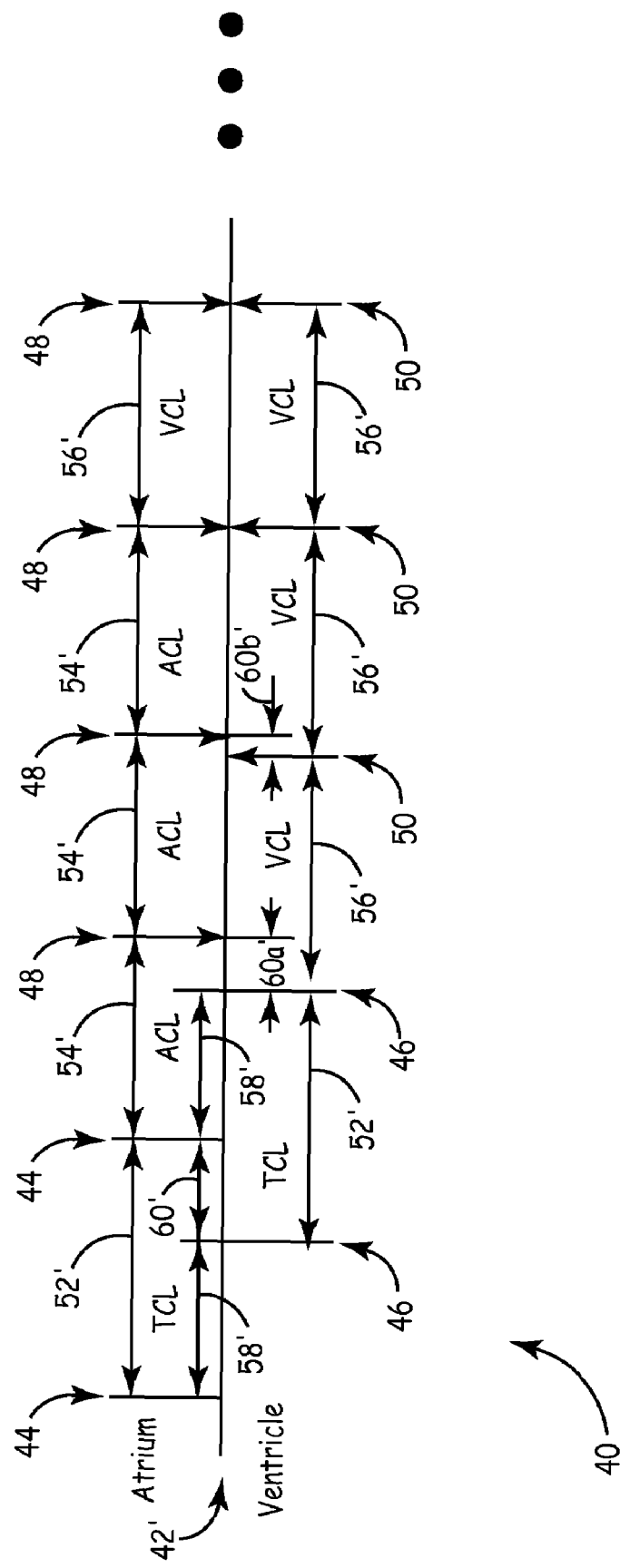
FIG. 3 is an exemplary timing diagram illustrating another technique used by the medical device of FIG. 1 for initially delivering anti-tachycardia pacing in the atrial and ventricular regions in accordance with certain embodiments of the invention.

FIGS. 2 and 3 show exemplary timing diagrams 40 and 40', respectively illustrating distinct techniques used by the IMD 10 of FIG. 1 for initially delivering anti-tachycardia pacing in the atrial and ventricular regions in accordance with certain embodiments of the invention. Such techniques, in certain embodiments, are provided via a controller within the IMD 10. With reference to FIG. 2, the timing diagram 40 includes a timeline 42, showing sensing and pacing of a patient's atrium on the upper portion of the timeline 42 and of a patient's ventricle on the lower portion of the timeline 42. Likewise, with respect to FIG. 3, the timing diagram 40' includes a timeline 42', showing sensing and pacing of a patient's atrium on the upper portion of the timeline 42'and of a patient's ventricle on the lower portion of the timeline 42'. As should be appreciated with respect to FIGS. 2 and 3, the sensed and paced atrium can involve either of the patient's atria and likewise, the sensed and paced ventricle can involve either of the patient's ventricles.

The atrial sense readings and pacing pulses shown in FIGS. 2 and 3 are respectively represented with solid lines and solid arrows on the upper portions of the timelines 42 and 42', with each line referenced as an Asense reading 44 and each arrow referenced as an Apace pulse 48. In certain embodiments, the Asense readings 44 and Apace pulses 48 are provided via one or more pace/sense electrodes of the IMD 10 positioned in the atrium. Conversely, the ventricle sense readings and pacing pulses shown in FIGS. 2 and 3 are respectively represented with solid lines and solid arrows on the lower portions of the timelines 42 and 42', with each line referenced as a Vsense reading 46 and each arrow referenced as a Vpace pulse 50. In certain embodiments, the Vsense readings 46 and Vpace pulses 50 are provided via one or more pace/sense electrodes of the IMD 10 positioned in the ventricle. The Asense readings 44 and Vsense readings 46 each represent sensed depolarizations of the corresponding heart region.

As shown in each of FIGS. 2 and 3, the initial cycles of Asense readings 44 and Vsense readings 46 are each interpreted as involving a tachycardia. With respect to FIG. 2, in certain embodiments, the cycle lengths of such tachycardias in the atrium and ventricle (TCL 52) have similar duration. Likewise, with respect to FIG. 3, in certain embodiments, the cycle lengths of such tachycardias in the atrium and ventricle (TCL 52') have similar duration. With respect to FIGS. 2 and 3, following such interpretation, a decision is made to initiate anti-tachycardia pacing in both the atrium and ventricle. The decision to initiate pacing, in certain embodiments, is made following the last Vsense reading 46. As described above, the anti-tachycardia pacing can be used as an initial method of treating the tachycardia. However, even if such pacing fails to terminate the tachycardia, this pacing can be used to identify the source of the tachycardia to prompt additional, yet more appropriate, therapy to be delivered in treating the patient.

FIGS. 2 and 3 respectively illustrate two techniques of initially delivering the anti-tachycardia pacing to a patient following detection by the IMD 10 of tachycardia in the sensed atrium and ventricle. In certain embodiments of each technique, the pacing is provided to the atrium and ventricle so that the corresponding Apace and Vpace pulses 48, 50 are initially delivered out of phase with each other. Each of the Apace pulses 48 are delivered so as to have cycle lengths (ACL 54 in FIG. 2, ACL 54' in FIG. 3) which are respectively shorter than the TCL 52 and TCL 52' so as to overdrive the atrium. Likewise, each of the Vpace pulses 50 are delivered so as to have cycle lengths (VCL 56 in FIG. 2, VCL 56' in FIG. 3) which are respectively shorter than the TCL 52 and TCL 52' so as to overdrive the ventricle. As described above, the Apace pulses 48 are initially delivered and each ACL 54 and 54' is set so as to avoid delivery of the Apace pulses 48 during the atrium's vulnerable period.

As should be appreciated, with respect to FIGS. 2 and 3, since the Apace and Vpace pulses 48 and 50 are delivered so as to be initially out of phase with each other, the corresponding ACLs 54, 54' and VCLs 56, 56' are, in turn, initially out of alignment on their respective timelines 42, 42'. However, in certain embodiments, the ACLs 54, 54' are distinct from the respective VCLs 56, 56'. As such, in certain embodiments as shown in FIGS. 2 and 3, over a series of pacing pulses in both the corresponding atrium and ventricle, such Apace pulses 48 can be gradually brought into phase with the Vpace pulses 50. As described above, such gradual shift enables one to continue to avoid delivery of Apace pulses 48 during the atrium's vulnerable regions, and ultimately results in simultaneous delivery of the pulses. Once the pulses are brought into phase with each other, in certain embodiments, as shown in FIGS. 2 and 3, the ACLs 54, 54' are respectively changed to VCLs 56, 56' so the Apace pulses 48 and the Vpace pulses 50 will continue to be delivered simultaneously for a number of pacing cycles, as described in the '248 application.

With respect to FIG. 2, each TCL 52 includes a Asense reading 44 to Vsense reading 46 interval (such being an initial AV interval, $AV_0$ interval 58) and a Vsense reading 46 to Asense reading 44 interval (such being an initial VA interval, $VA_0$ interval 60). As shown, the duration of the $AV_0$ interval 58 is less than the duration of the $VA_0$ interval 60. In certain embodiments, as exemplified herein, cases in which a tachycardia has such a shorter $AV_0$ interval can lead to a determination that the initial pacing technique depicted in FIG. 2 is more efficient over the pacing technique depicted in FIG. 3. Such determination, in certain embodiments, is provided via a controller within the IMD 10. As such, the pacing technique depicted in FIG. 2 would be initiated so that the AV interval is gradually "shrunk" during the initial pacing bursts of the anti-tachycardia pacing in order to more efficiently bring the Apace pulses 48 into phase with the Vpace pulses 50.

As described above with respect to FIG. 2, the Apace pulses 48 and Vpace pulses 50 are delivered having respective ACL 54 and VCL 56, both of which are shorter in duration than the TCL 52. In certain embodiments, to shrink the AV interval over the pacing bursts of the anti-tachycardia pacing, the ACL 54 is made greater than the VCL 56.

As can be appreciated from FIG. 2, the difference between the ACL 54 and the VCL 56 is the increment by which the AV intervals is shortened over the timeline 42. As such, in specifically designating the ACL 54 and the VCL 56, one would use the following equation to determine a corresponding number of pacing cycles that would need to be used before the AV interval is eliminated and, in turn, the Apace and Vpace purses 48, 50 are brought into phase with each other:

$$N = CEIL((AV/(ACL-VCL))-1), \quad (1)$$

where CEIL indicates a rounding up of any fractional amount calculated. In use, for example, if the ACL 54 is designated as being 50 is larger than the VCL 56 (ACL−VCL=50 ms), and the AV interval is measured as 150 ms, the equation would result in N=CEIL ((150/50)−1), or N=2.

Conversely, if a quantity of initial pacing cycles is provided up front (e.g., N=2), one can designate one of the ACL 54 or the VCL 565 and subsequently determine (using equation (1) above) the other of the ACL 54 or the VCL 56, By subsequently using the determined ACL 54 or VCL 56, the technique can be configured for eliminating the AV interval and, in turn, bringing the Apace and Vpace pulses 48, 50 in phase, over the provided quantity of initial pacing cycles. For example, equation (1) can be reconfigured to:

$$ACL=(AV+(VCL\times N)+VCL)/(N+1). \qquad (2)$$

In use, if the quantity of initial pacing cycles is provided up front as two (N=2), the AV interval is measured as 150 ms, and the VCL 56 is designated as 400 ms, the equation would result in ACL=(150 ms+(400 ms×2)+400 ms)/(2+1), or ACL=450 ms. This is representatively depicted in FIG. 2, wherein the AV interval is decreased gradually and in equal decrements across the timeline 42 over two initial pacing cycles, from the $AV_0$ interval 58 measured at the TCL 52 to an eventual elimination of the AV interval altogether. With specific reference to FIG. 2, following initial delivery of an initial Apace pulse 48 and Vpace pulse 50, the AV interval is decreased from the $AV_0$ interval 58 to an AV interval 58a, with the AV interval 58a being two-thirds the duration of the $AV_0$ interval 58. Following a subsequent delivery of one each of the Apace and Vpace pulses 48 and 50, the AV interval is further decreased from the AV interval 58a to an AV interval 58b, with the AV interval 58b being one-third the duration of the $AV_0$ interval 58. As shown, upon a further delivery of one each of the Apace and Vpace pulses 48 and 50, the pacing pulses are provided in phase with each other. Immediately following this alignment, the ACL 54 is changed to the VCL 56 so that subsequent pacing deliveries of the Apace pulses 48 and the Vpace pulses 50 continue to be delivered simultaneously.

With reference to FIG. 3, each TCL 52' includes an Asense reading 44 to Vsense reading 46 interval (such being an initial AV interval, $AV_0$ interval 58') and a Vsense reading 46 to Asense reading 44 interval (such being an initial VA interval, $VA_0$ interval 60'). As shown, the duration of $AV_0$ interval 58' is greater than the duration of $VA_0$ interval 60'. In certain embodiments, as exemplified herein, cases in which a tachycardia has such a shorter $VA_0$ interval can lead to a determination that the initial pacing technique depicted in FIG. 3 is more efficient over the pacing technique depicted in FIG. 2. Such determination, in certain embodiments, is provided via a controller within the IMD 10. As such, the pacing technique depicted in FIG. 3 would be initiated so that the VA interval is gradually "shrunk" during the initial pacing bursts of the anti-tachycardia pacing in order to more efficiently bring the Apace pulses 48 into phase with the Vpace pulses 50.

As described above with respect to FIG. 3, the Apace pulses 48 and Vpace pulses 50 are respectively delivered having respective ACL 54' and VCL 56', both of which are shorter in duration than the TCL 52'. In certain embodiments, to shrink the VA interval over the pacing bursts of the anti-tachycardia pacing, the VCL 56' is made greater than the ACL 54'.

Similar to that described above with respect to FIG. 2, as can be appreciated from FIG. 3, the difference between the VCL 56' and the ACL 54' is the increment by which the VA interval is shortened over the timeline 42'. As such, in specifically designating the VCL 56' and the ACL 54', one would use the following equation to determine a corresponding number of pacing cycles that would need to be used before the VA interval is eliminated and, in turn, the Apace and Vpace pulses are brought into phase with each other:

$$N=CEIL((VA/(VCL-ACL))-1), \qquad (3)$$

where CEIL indicates a rounding up of any fractional amount calculated. In use, for example, if the VCL 56' is designated as being 50 ms larger than the ACL 54' (VCL−ACL=50 ms), and the VA interval is measured as 150 ms, the equation would result in N=CEIL ((150/50)−1), or N=2.

Conversely, if a quantity of initial pacing cycles is provided up front (e.g., N=2), one can designate one of the VCL 56' or the ACL 54', and subsequently determine (using equation (3) above) the other of the VCL 56' or the ACL 54'. By subsequently using the determined VCL 56' or ACL 54, the technique can be configured for eliminating the VA interval and, in turn, bringing the Apace and Vpace pulses 48, 50 in phase, over the provided quantity of initial pacing cycles. For example, equation (3) can be reconfigured to:

$$ACL=((VCL\times N)+VCL-VA)/(N+1). \qquad (4)$$

In use, if the quantity of initial pacing cycles is provided up front as two (N=2), the VA interval is measured as 150 ms, and the VCL 56 is designated as 400 ms, the equation would result in ACL=((400 ms×2)+400 ms 150 ms)/(2+1), or ACL=350 ms. This is representatively depicted in FIG. 3, wherein the VA interval is decreased gradually and in equal decrements across the timeline 42' over two initial pacing cycles, from the $VA_0$ interval 60' measured at the TCL 52' to an eventual elimination of the VA interval altogether. With specific reference to FIG. 3, following initial delivery of an initial Apace pulse 48, the VA interval is decreased from the $VA_0$ interval 60' to a VA interval 60a', with the VA interval 60a' being two-thirds the duration of the $VA_0$ interval 60'. Following a subsequent delivery of one each of the Apace and Vpace pulses 48 and 50, the VA interval is further decreased from the VA interval 60a' to a VA interval 60b', with the VA interval 60b' being one-third the duration of the $VA_0$ interval 60'. As shown, upon a further delivery of one each of the Apace and Vpace pulses 48 and 50, the pacing pulses are provided in phase with each other. Immediately following this alignment, the ACL 54' is changed to the VCL 56' so that subsequent pacing deliveries of the Apace pulses 48 and the Vpace pulses 50 continue to be delivered simultaneously.

As mentioned above with respect to FIGS. 2 and 3, while not shown, following alignment of the pacing pulses, such Apace and Vpace pulses 48, 50 continue to be delivered simultaneously for a number of pacing pulses, as described in the '248 application. In certain embodiments, as described above with respect to the '248 application, there may be as many as ten simultaneous pacings delivered before a blanking period. However, it should be appreciated that the number of simultaneous pacings would be limited, if possible. In doing such, one would want to entirely capture the heart via such pacing, yet not delay further therapy being delivered to the heart, if necessary. In certain embodiments, the number of simultaneous pacings would generally be between two and ten, and most often, between two and five.

Further, when using a similar increment for shrinking the AV and VA intervals, as shown in the respective techniques of FIGS. 2 and 3, it should be appreciated that one less Vpace pulse 50 is needed during the gradual shortening of the VA interval using the technique of FIG. 3. In turn, there is one less VCL 56' exhibited an FIG. 3 during such time as well. Consequently, even though a similar number of ACLs 54 and ACLs 54' are used during the respective AV and VA shortening periods of the initial pacing techniques depicted in FIGS. 2 and 3, since the ACLs 54' are shorter in duration than the VCLs 56' in FIG. 3, the pacing technique depicted in FIG. 3 can be used to provide quicker alignment of the Apace and Vpace pulses 48 and 50.

Even though FIGS. 2 and 3 each depict techniques by which the Apace pulses 48 are gradually brought into phase with the Vpace pulses 50 (using the ventricular chamber as the chamber of synchronization), the invention should not be limited to such. Specifically, any of a number of variations of such methods could be used. For example, the Vpace pulses 50 could just as well be gradually brought into phase with the Apace pulses 48 using variations of the above methods and still fall within the spirit of the invention. In addition, the change in the internal length (ACL in FIG. 2, VCL in FIG. 3) need not be constant. The change of the interval length could increase or decrease over one or more cardiac cycles.

Figure 4:
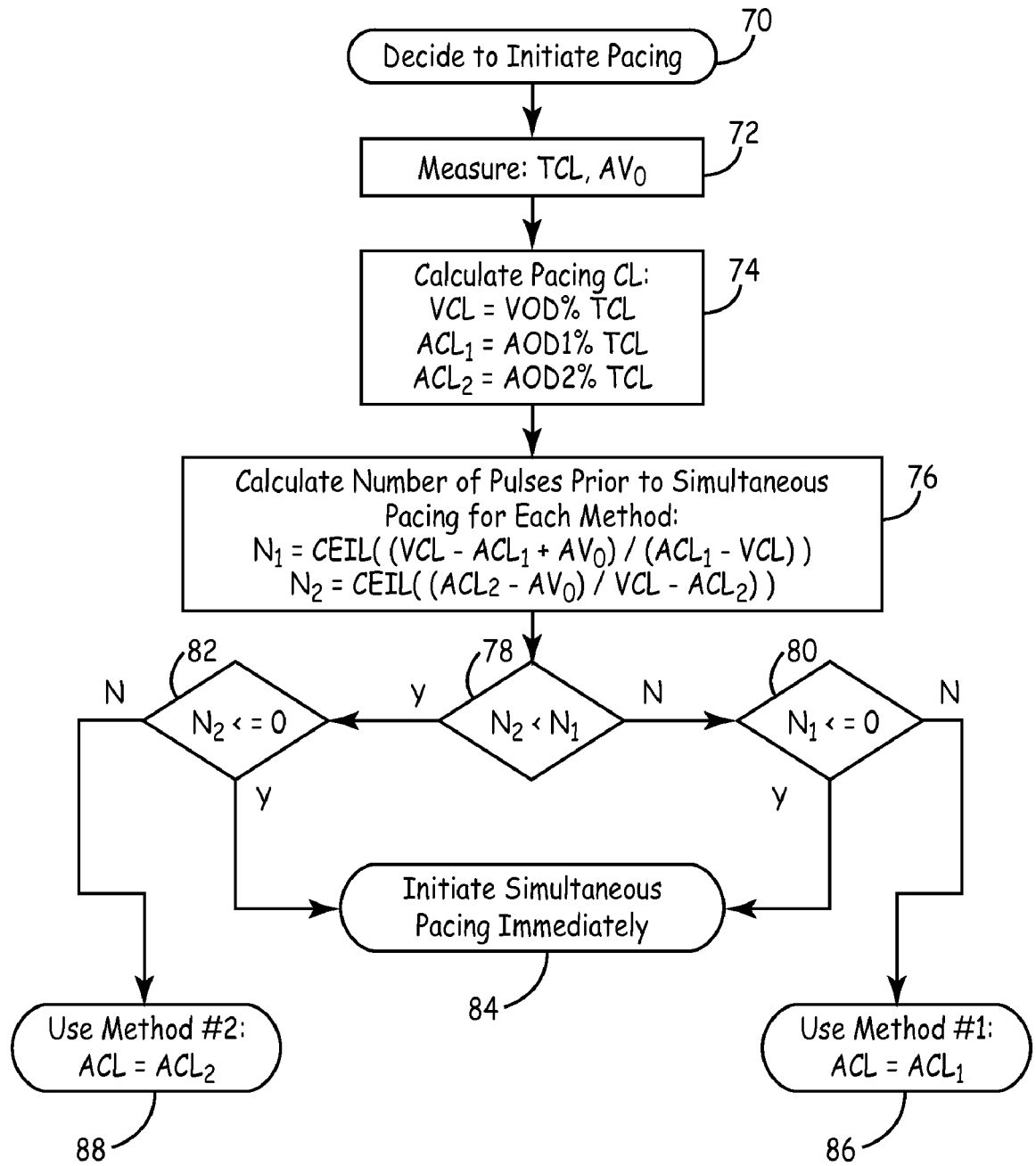
FIG. 4 is a flowchart illustrating an exemplary method used by the medical device of FIG. 1 for choosing the more efficient of the two initial pacing methods illustrated in FIGS. 2 and 3 given any tachycardia event in accordance with certain embodiments of the invention.

FIG. 4 is a flowchart illustrating an exemplary method for determining which initial anti-tachycardia pacing technique depicted in FIG. 2 and FIG. 3 is more efficient, given a tachycardia event being interpreted in the atrial and ventricular regions. In certain embodiments, such method steps are performed via a controller of the IMD 10. As described below, FIG. 4 provides a method of calculating the quantity of pacing pulses needed before the Apace pulses 48 are brought into phase with the Vpace pulses 50 using both the initial pacing techniques depicted in FIGS. 2 and 3. Whichever technique results in a lower quantity of pacing pulses being needed is the preferred, and in turn, selected technique. Because the techniques depicted in FIGS. 2 and 3 may be varied as exemplified herein (e.g., Vpace pulses 50 may be brought into phase with the Apace pulses 48), it should be appreciated the flowchart steps described herein may also be varied to encompass such variations as well, and still fall within the embodiments of the invention.

An initial step 70 of FIG. 4 involves the decision to initiate anti-tachycardia pacing. Such decisions, in certain embodiments as described above with respect to FIGS. 2 and 3, is reached upon detection of a tachycardia in the atrial and/or ventricular regions. As also described above, in certain embodiments such decision to initiate pacing decision occurs at the last Vsense reading 46 on the timelines 42, 42'. Upon determining that anti-tachycardia pacing is appropriate, certain measurements are initially made with respect to the tachycardia in step 72 before the pacing is initiated. In certain embodiments, these measurements include determining the tachycardia cycle length (TCL) and the Asense to Vsense interval of the TCL (such being the initial AV interval, $AV_0$). For example, these parameters are shown in FIG. 2 for the corresponding tachycardia as TCL 52 and AV 58. As shown in FIG. 2, in certain embodiments, the $AV_0$ can be a small percentage of the TCL (e.g., less than 50% of the TCL). For example, the TCL can be 500 ms and the AV % can be 150 ms (30% of the TCL). In such embodiments, it should be appreciated that the small $AV_0$ would thereby correspond to the Vsense to Asense interval of the TCL (such being the initial VA interval, $VA_0$) being a large percentage of the TCL (e.g., greater than 50% of the TCL). Using the exemplary values above, with the TCL being 500 ms and the $AV_0$ being 150 ms, the $VA_0$ would be 350 ms (70% of the TCL). As such, the $AV_0$ is less than the $VA_0$, and as previously suggested herein, the initial pacing technique depicted in FIG. 2 is likely the preferred technique for the particular tachycardia. This can be confirmed in the further steps of the flowchart of FIG. 4.

Step 74 involves calculating the pacing cycle lengths VCL, $ACL_1$, and $ACL_2$. As described above, the ventricle cycle length (VCL) of the Vpace pulses 50 is designated as some lower percentage of the TCL. Based on the designated VCL, the atrium cycle lengths $ACL_1$ and $ACL_2$ are respectively provided for the initial pacing techniques depicted in FIGS. 2 and 3. The technique of FIG. 2 warrants the ACL being greater in duration than the VCL yet less than the TCL. As such, the $ACL_1$ is so designated. The technique of FIG. 3 warrants the ACL being less than the VCL. As such, the $ACL_2$ is so designated. In certain embodiments, each of the VCL, $ACL_1$, and $ACL_2$ may be designated as being in a range of 70% to 90% of the TCL; however, the invention should not be limited to such as the VCL, $ACL_1$, and $ACL_2$ can be designated and varied as desired (so long as the above conditions concerning VCL, $ACL_1$, and ACL are met, and the VCL, $ACL_1$, and $ACL_2$ do not lead to pacing pulses being delivered in the vulnerable regions of the cardiac cycle). In certain embodiments, one or more sets of the pacing cycle lengths VCL, $ACL_1$, and $ACL_2$ can be pre-programmed within a processor of the IMD 10, with each set corresponding to different measured values of the TCL. For example, for a measured TCL value of 500 ms, the VCL can be programmed as being 400 ms (80% of the TCL), the ACL can be programmed as being 450 ms (90% of TCL), and the $ACL_2$ can be programmed as being 350 ms (70% of TCL). In other certain embodiments, the processor can be programmed with certain percentages of the TCL for each of the VCL, $ACL_1$, and $ACL_2$ values. As such, following measurement of a TCL value, the VCL, $ACL_1$, and $ACL_2$ values can be calculated using the percentages.

Step 76 involves using a pair of equations to determine the number of initial pacing cycles needed to provide simultaneous pacing via the initial pacing techniques depicted in FIGS. 2 and 3. The pair of equations for determining the number of pacing cycles for the techniques depicted in FIGS. 2 and 3 are respectively:

$$N_1 = CEIL((VCL - ACL_1 + AV_0)/(ACL_1 - VCL)) \text{ and} \quad (5)$$

$$N_2 = CEIL((ACL_2 - AV_0)/(VCL - ACL_2)), \quad (6)$$

where CEIL indicates a rounding up of any fractional amount calculated. Using the values provided above, $N_1 = CEIL((400-450+150)/(450-400)) = 2$ and $N_2 = CEIL((350-150)/(400-350)) = 4$.

Step 78 involves a comparison of the calculated values $N_1$ and $N_2$. If $N_1$ is not greater than $N_2$, one is directed to step 80. However, if $N_1$ is greater than $N_2$, one is directed to step 82. Using the $N_1$ and $N_2$ values calculated above ($N_1 = 2$ and $N_2 = 4$), $N_1$ is not greater than $N_2$, so one is directed to step 80. Step 80 involves a determination of whether $N_1$ is less than or equal to zero. If $N_1$ is less than or equal to zero, no pacing cycles are needed prior to the start of simultaneous pacing as pacing pulses simultaneously delivered in both the atrium and ventricle will fall outside the vulnerable regions of the cardiac cycle. As such, one is directed to step 84, in which simultaneous anti-tachycardia pacing is initiated immediately. Conversely, if in step 80, $N_1$ is not found to be less than or equal to zero, one is directed to step 86, in which the initial pacing technique depicted in FIG. 2 is carried out using $ACL_1$ as the ACL 54 with the $N_1$ value indicating the quantity of pacing cycles warranted before the atrium and ventricular pacing pulses are delivered in phase with each other. Using the $N_1$ value calculated above ($N_1 = 2$), a quantity of two pacing cycles are necessary before the pacing pulses are delivered in phase. This is demonstrated in FIG. 2, as described above.

As mentioned above, the flowchart of FIG. 4 is used to determine which pacing technique depicted in FIGS. 2 and 3 is most efficient, given a tachycardia event being interpreted in the atrial and ventricular regions. As such, with every tachycardia event, the TCL and $AV_0$ values measured in step 72 may differ. For example, the <measured value of the TCL can be 450 ms (differing from the 500 ms measured in the case exemplified above). Such TCL and $AV_0$ parameters are shown in FIG. 3 for the corresponding tachycardia as TCL 52' and $AV_0$ 58'. As shown in FIG. 3, in certain embodiments, the $AV_0$ value can be a large percentage of the TCL (e.g., greater than 50% of the TCL). For example, the $AV_0$ can be 300 ms (about 67% of the TCL). In turn, the $VA_0$ of the TCL would be a small percentage of the TCL (e.g., less than 50% of the TCL). With the TCL being 450 ms and the $AV_0$ being 300 ms, the $VA_0$ would be 150 ms (about 33% of the TCL). As such, the $VA_0$ is less than the $AV_0$, and as previously suggested herein, the initial pacing technique depicted in FIG. 3 is likely the preferred technique for the particular tachycardia. This can be confirmed in the further steps of the flowchart of FIG. 4.

Having measured the TCL and $AV_0$ values as 450 ms and 300 ms respectively in step 72, one is directed to step 74 to calculate the pacing cycle lengths, VCL, $ACL_1$, and $ACL_2$. In certain embodiments, the values provided above for VCL, $ACL_1$, and $ACL_2$ may remain the same as already described if the TCL for the tachycardia event in the atrial and ventricular regions is similar in duration to what has been exemplified above. However, in certain embodiments, as described with this case, since the TCL is 450 ms (differing from the TCL value of 500 ms measured in the above case), it should be appreciated that the corresponding values for the VCL, $ACL_1$, and $ACL_2$ would need to be different from what was described above. As described above, the designated VCL, $ACL_1$, and $ACL_2$ values would be less than the TCL, while the $ACL_1$ would be greater than the VCL and the VCL would be greater than the $ACL_2$. For example, the VCL can be designated as being 375 ms (about 83% of the TCL), the $ACL_1$ can be programmed as 400 ms (about 89% of TCL) and the $ACL_2$ can be programmed as 350 ms (about 78% of TCL).

In turn, the number of pacing cycles needed to provide simultaneous pacing via the initial pacing techniques depicted in FIGS. 2 and 3 are calculated in step 76. Using equations (5) and (6) shown above and the values for TCL (450 ms), $AV_0$ (300 ms), VCL (375 ms), $ACL_1$ (400 ms), and $ACL_2$ (350 ms) described above, $N_1$=CEIL ((375−400+300)/(400−375))=11 and $N_2$=CEIL ((350−300) (375−350))=2. In going on to step 78, it is found that $N_1$ is greater than $N_2$. As such, one is directed to step 82. Step 82 involves a determination of whether $N_2$ is less than or equal to zero. Again, like in step 80 described above, if $N_2$ is less than or equal to zero, no pacing cycles are needed prior to the start of simultaneous pacing as pacing pulses simultaneously delivered in both the atrium and ventricle will fall outside the vulnerable regions of the cardiac cycle. As such, one is directed to step 84, in which simultaneous anti-tachycardia pacing is initiated immediately. Conversely, if in step 82, $N_2$ is not found to be less than or equal to zero, one is directed to step 88, in which the initial pacing method depicted in FIG. 3 is carried out using $ACL_2$ as the ACL 54' with the $N_2$ value indicating the quantity of pacing cycles warranted before the atrium and ventricular pacing pulses are delivered in phase with each other. Using the $N_2$ value calculated above ($N_2$=2), a quantity of two pacing cycles are necessary before the pacing pulses are delivered in phase. This is demonstrated in FIG. 3, as described above.

As described above, upon being directed to step 84, simultaneous anti-tachycardia pacing is initiated immediately. In immediately delivering such simultaneous pacing, one should appreciate that the flowchart calculations of FIG. 4 have provided an indication that there is no risk of inducing atrial tachyarrhythmia. However, in certain embodiments, such pacing can instead involve immediate delivery of an Apace pulse 48 followed by simultaneous pacing in subsequent pacing cycles. This initial single Apace pulse 48 has been found to improve control of the atrium prior to the initiation of the simultaneous pacing.

A further technique of providing simultaneous anti-tachycardia pacing in the atrial and ventricular regions while avoiding atrial proarrhythmia is described below with respect to FIGS. 5-7. Such technique, in certain embodiments, is provided via a controller within the IMD 10. In certain embodiments, this technique involves the introduction of a "no pacing" window for the atrium. This window generally represents the vulnerable region of the cardiac cycle for the atrium following the start of its depolarization. Depending on the cycle length of the tachycardia (TCL), the size of the vulnerable period can generally be estimated. For example, in certain embodiments when the TCL is 500 ms, the vulnerable region of the atrium can be estimated to begin 100 ms following the start of the atrium's depolarization and can end 300 ms following the start of atrium's depolarization. As such, based on measured parameters of the TCL and the designated ventricular cycle length used in the anti-tachycardia pacing (VCL), one can effectively predict if pacing pulses delivered simultaneously will be delivered in such window. If such pulses would not be delivered in the window, simultaneous pacing can be immediately initiated. Conversely, if such pulses would be delivered in the window, the initial pacing approaches depicted in FIGS. 2 and 3 can be utilized.

Figure 5:
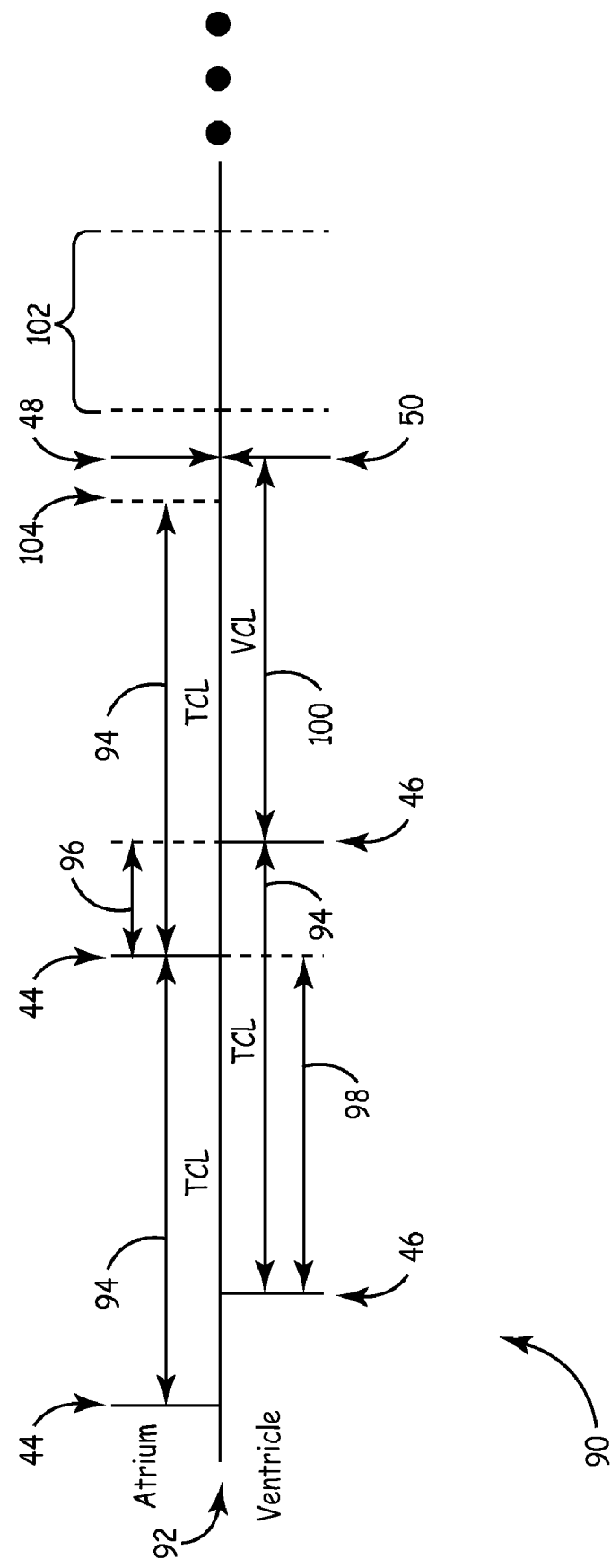
FIG. 5 illustrates an exemplary timing diagram illustrating a technique used by the medical device of FIG. 1 for verifying that anti-tachycardia pacing can be delivered simultaneously in the atrial and ventricular regions without delivery within a vulnerable region of the cardiac cycle of the atrium in accordance with certain embodiments of the invention.
Figure 6:
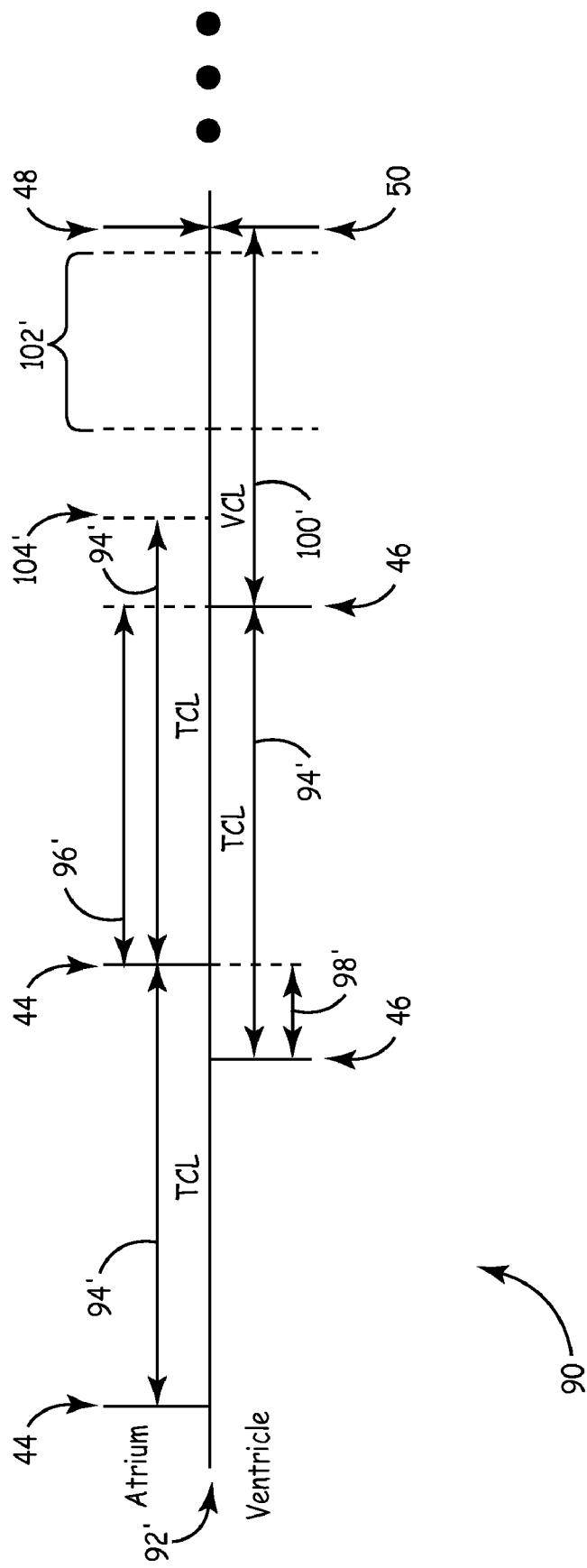
FIG. 6 illustrates an exemplary timing diagram illustrating another technique used by the medical device of FIG. 1 for verifying that anti-tachycardia pacing can be delivered simultaneously in the atrial and ventricular regions without delivery within a vulnerable region of the cardiac cycle of the atrium in accordance with certain embodiments of the invention.
Figure 7:
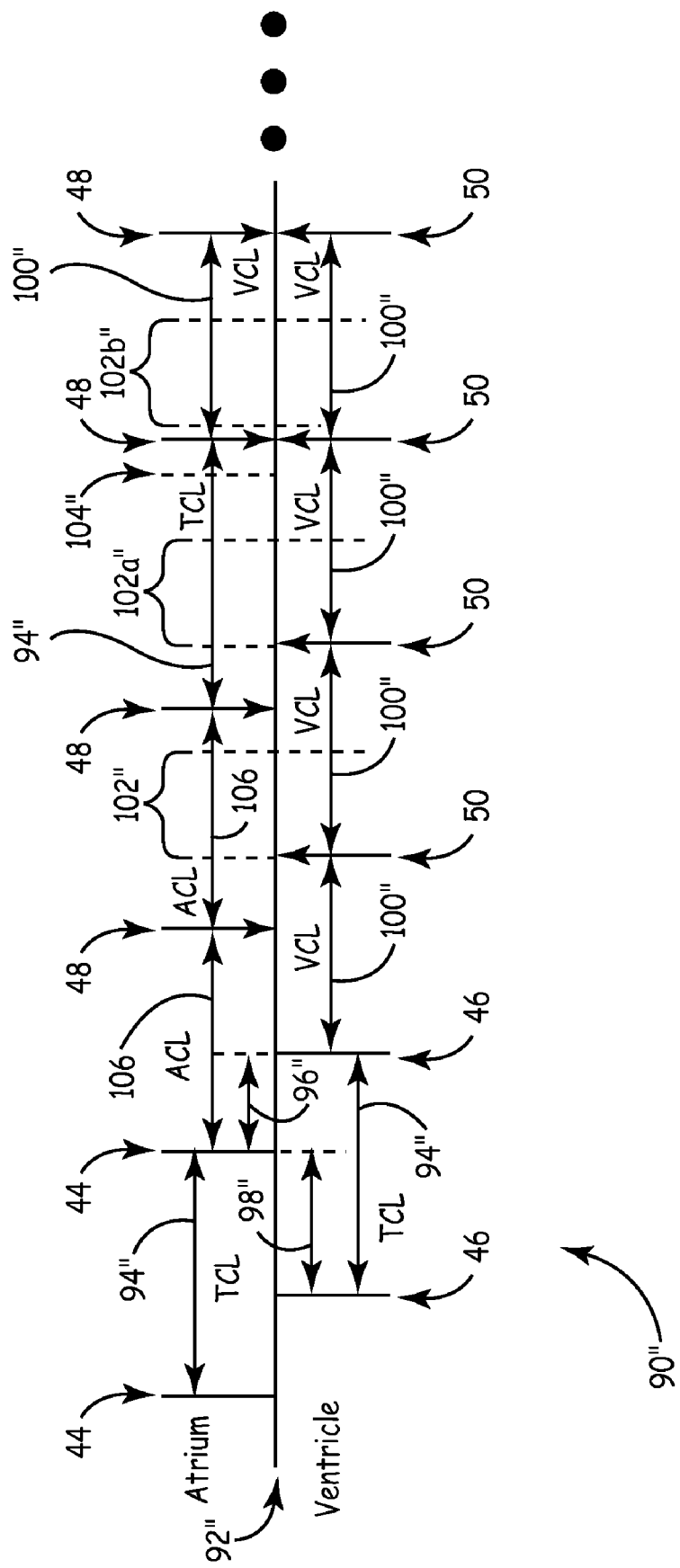
FIG. 7 illustrates an exemplary timing diagram illustrating the technique depicted in FIG. 5 with the technique depicted in FIG. 2 in accordance with certain embodiments of the invention.

FIGS. 5, 6, and 7 show timing diagrams 90, 90', and 90'' respectively, each illustrating distinct depictions of this further technique implemented via the IMD 10 of FIG. 1 in accordance with certain embodiments of the invention. Similar to FIGS. 2 and 3, FIGS. 5, 6, and 7 respectively include timelines 92, 92', and 92'', each showing Asense readings 44 and Apace pulses 48 of a patient's atrium on the upper portions of the timelines 92, 92', 92'' and Vsense readings 46 and Vpace pulses 50 of a patient's ventricle on the lower portions of the timelines 92, 92', 92''. As shown in each of FIGS. 5, 6, and 7, the initial cycles of Asense readings 44 and Vsense readings 46 are interpreted as involving tachycardias. With respect to FIGS. 5, 6, and 7, in certain embodiments, the cycle lengths of such tachycardias in the atriums and ventricles (respectively TCL 94, 94', and 94'') have similar durations respectively on the timelines 92, 92', and 92''. In addition, each TCL 94, 94', and 94'' includes a Asense reading 44 to Vsense reading 46 interval ($AV_0$ interval 96, 96', and 96'' respectively) and Vsense reading 46 to Asense reading 44 interval (VA interval 98, 98', and 98'' respectively). Finally, in delivering the anti-tachycardia pacing to a patient following detection by the IMD 10 of the tachycardias, each of the Apace pulses 48 and Vpace pulses 50 are delivered corresponding to certain cycle lengths which are respectively shorter than the respective TCLs 94, 94', and 94'' so as to overdrive the corresponding heart regions. Specifically, the Vpace pulses 50 are shown in FIGS. 5, 6, and 7 to have respective cycle lengths (VCL 100, VCL 100', VCL 100'').

With respect to FIG. 5, the $AV_0$ interval 96 is less than the $VA_0$ interval 98. In turn, as is illustrated the Vpace pulse 50 would be delivered proximate to the beginning of the "no pacing" window 102. Using the TCL 94, the $AV_0$ and the VCL 100 parameters, one can determine where the initial Vpace pulse 50 will be delivered in relation to the window 102. This can be determined with the following calculation:

$$AV_{n-1} + VCL - TCL < AVP_{MIN}, \qquad (7)$$

where $AVP_{MIN}$ is the beginning of the window 102 on the timeline 92 measured from the expected depolarization of the atrium 104 for that cardiac cycle. If equation (7) is true, the Vpace pulse 50 is delivered outside the window 102 and simultaneous pacing of both the atrium and ventricle can be initiated immediately.

As described above, in certain embodiments, $AVP_{MIN}$ is 100 ms. Since the Vpace pulse 50 is in the first pacing cycle, n=1. The values of the other parameters, for example, can be 500 ms for the TCL 94, 125 ms for the $AV_0$ interval 96, and 425 ms for the VCL 100. Based on these exemplary values, the equation would result in 125+425−500<100, or 50<100. As such, the equation is true, and simultaneous delivery of the Apace and Vpace pulses 48, 50 can be initiated without risk of inducing atrial tachycardia. This is because the Apace pulse 48 would be delivered outside the atrium's vulnerable region of the cardiac cycle.

With respect to FIG. 6, the $AV_0$ interval 96 is greater than the $VA_0$ interval 98'. In turn, as illustrated, the Vpace pulse 50 would be delivered proximate to the end of the "no pacing" window 102'. Similar to the calculation used with the tachycardia exemplified in FIG. 6, using the TCL 94', the $AV_0$ 96', and the VCL 100' parameters, one can determine where the initial Vpace pulse 50 will be delivered in relation to the window 102'. This can be determined with the following calculation:

$$AV_{n-1}+VCL-TCL>AVP_{MAX}, \qquad (8)$$

where $AVP_{MAX}$ is the end of the window 102' on the timeline 92' measured from the expected depolarization of the atrium 104' for that cardiac cycle. If equation (8) is true, the Vpace pulse 50 is delivered outside the window 102' and simultaneous pacing of both the atrium and ventricle can be initiated immediately.

As described above, in certain embodiments, $AVP_{MAX}$ is 300 ms. Since the Vpace pulse 50 is in the first pacing cycle, n=1. The values of the other parameters for example, can be 500 ms for the TCL 94', 400 ms for the $AV_0$ interval 96' and 425 ms for the VCL 100'. Based on these exemplary values, the equation would result in 400+425−500>300, or 325>300. As such, the equation is true, and simultaneous delivery of the Apace and Vpace pulses 48, 50 can be initiated without risk of inducing atrial tachycardia. This is because the Apace pulse 48 would be delivered outside the atrium's vulnerable region of the cardiac cycle.

FIG. 7 illustrates the further technique being used in conjunction with the initial pacing technique depicted in FIG. 2. For example, as shown, the $AV_0$ interval 96" is less than the $VA_0$ interval 98". In turn, as illustrated, the Vpace pulse 50 will be delivered proximate to the end of the "no pacing" window 102". Using the TCL 94", the AV 96", and the VCL 100" parameters, one can determine where the initial Vpace pulse 50 will be delivered in relation to the window 102". Again, this can be determined with the equation (7) provided above. As noted above with respect to FIG. 5, if equation (7) is true, the Vpace pulse 50 is delivered outside the window 102" and simultaneous pacing of both the atrium and ventricle can be initiated immediately.

As described above, in certain embodiments, $AVP_{MIN}$ is 100 ms. Since the Vpace pulse 50 is in the first pacing cycle, n=1. The values of the other parameters, for example, can be 500 ms for the TCL 94', 200 ms for the $AV_0$ interval 96", and 425 ms for the VCL 100". Based on these exemplary values, the equation would result in 200+425−500<100, or 125<100. As such, the equation is false, and simultaneous delivery of the Apace and Vpace pulses 48, 50 cannot be initiated without risk of inducing atrial tachycardia. This is shown in FIG. 7, where the initial Vpace 50 is delivered within the window 102". In turn, one of the techniques depicted in FIGS. 2 and 3 would be used to gradually shift the pacing pulses 48, 50 into phase with each other. As stated above, since the $AV_0$ interval 96" is less than the $VA_0$ interval 98", the pacing technique of FIG. 2 is likely the preferred technique for the particular tachycardia. The flowchart in FIG. 4, as described herein, can be used to confirm this.

Using FIG. 4 for the tachycardia event interpreted in FIG. 7, the decision to initiate pacing has already been made for step 70 and the values for TCL 94" (500 ms) and $AV_0$ interval 96" (200 ms) have already been measured for step 72. In addition, the parameters for VCL (VCL 100" being 425 ms) and the $ACL_1$ (ACL 106 being 450 ms) have already been calculated for step 74. Based on $ACL_1$ being 450 ms and VCL being 400 ms, $ACL_2$ would likely be 375 ms. As such, proceeding to step 76 and using equations (5) and (6) provide above, $N_1$ would equal (425−450+200)/(450−425), or 7, and $N_2$ would equal (400−200)/(425−400), or 8. In step 78, $N_2$ is not less than $N_1$, and in step 80, $N_1$ is not equal to or less than zero. As such, proceeding to step 86, the initial pacing technique depicted in FIG. 2 is used, with $ACL_1$=ACL 106=450 ms and number of pacing cycles being 7.

Therefore, an initial pacing cycle is provided using the pacing technique depicted in FIG. 2. As would be expected from the description above, the resulting AV internal would shrink by the difference between the ACL 106 and the VCL 100" (25 ms). As such, the AV interval after the initial pacing cycle would be 175 ms. Following delivery of the initial Vpace pulse 50, one can determine where a second Vpace pulse 50 will be delivered in relation to the window 102a" in order to see whether simultaneous pacing can be initiated. Again, this is determined with the equation (7) provided above. $AVP_{MIN}$ remains 100 ms, but since the second pacing cycle in involved, n=2. As described above, $AV_1$ is 175 ms. The values of the other parameters would remain 500 ms for the TCL 94', 450 ms for the ACL 106, and 425 ms for the VCL 100". Based on these exemplary values, the equation (7) would result in 175+425−500<100, or 100<100. As such, the equation is false, and simultaneous delivery of the Apace and Vpace pulses 48, 50 still cannot be initiated without risk of inducing atrial tachycardia. This is shown in FIG. 7, where the second Vpace 50 is delivered within the window 102a".

Therefore, a second pacing cycle is provided using the pacing technique depicted in FIG. 2. As would be expected from the description above, the resulting AV interval is again shrunk by the difference between the ACL 106 and the VCL 100" (25 Ms) As such, the AV interval after the second pacing cycle is 150 ms. Following delivery of the second Vpace pulse 50, one can determine where a third Vpace pulse 50 will be delivered in relation to the window 102b". Again, this is determined with the equation (7) provided above. $AVP_{MIN}$ remains 100 ms, but since the third pacing cycle is involved, n=3. As described above, $AV_2$ is 150 ms. The values of the other parameters would remain 500 ms for the TCL 94', 450 ms for the ACL 106, and 425 ms for the VCL 100". Based on these exemplary values, the equation (7) would result in 150+425−500<100, or 75<100. As such, the equation is true, and simultaneous delivery of the Apace and Vpace pulses 48, 50 can be initiated without risk of inducing atrial tachycardia. This is because the corresponding Apace pulse 48 would be delivered outside the atrium's vulnerable region of the cardiac cycle, as shown in FIG. 7.

Additionally, based on FIG. 7 and the related description, it should be appreciated that a tachycardia could be encountered having an $AV_0$ interval that is greater than the $VA_0$ interval, as exemplified in FIGS. 3 and 6. As such, using the further technique, one would use the corresponding TCL, $AV_0$, and VCL parameters in equation (8) as exemplified in FIG. 6 to determine where the initial Vpace pulse 50 would be delivered in relation to the "no pacing" window. If the pulse was determined to fall within the window, one of the techniques depicted in FIGS. 2 and 3 would be used to gradually shift the pacing pulses 48, 50 into phase with each other so as to provide for simultaneous delivery of the pulses 48, 50. As stated above, if the $AV_0$ interval is greater than the $VA_0$ interval, the pacing technique of FIG. 3 is likely the preferred technique for the particular tachycardia, but the flowchart in FIG. 4 can be used to confirm this. If the technique of FIG. 3 is determined to be the most efficient technique, as described above, the VA interval is gradually shrunk instead of the AV interval. As such, the pacing technique depicted in FIG. 3 will be implemented in a fashion similar to what is described in FIG. 7, with a determination being made after each pacing cycle to determine whether simultaneous pacing can be initiated.

It should be appreciated that the further technique described above with respect to FIGS. 5, 6, and 7 can be implemented in a variety of ways. For example, with respect to the tachycardias of FIGS. 5, 6, and 7 or any other tachycardia for that matter, one could simply use both equations (7) and (8) in determining where the next Vpace pulse 50 would be delivered with respect to the "no pacing" window. Determining which equation (7) or (8) is most applicable using the $AV_0$ and $VA_0$ intervals prior to using one or more of the equations, as described above, is but one implementation of the technique. In turn, such is not provided so as to limit the invention.

In addition, it should be appreciated that the above technique of FIGS. 5, 6, and 7 can be varied so that one determines whether an initial Apace pulse 48 (instead of the Vpace pulse 50) will be delivered in a "no pacing" window with respect to the ventricle (instead of the atrium). In certain embodiments, such "no pacing" window with respect to the ventricle may occur within the cardiac cycle about 130 ms to 400 ms after the ventricular depolarization. For example, using equations similar to what are provided above as equations (7) and (8), if a determination is made that such Apace pulse 48 falls outside such ventricle "no pacing" window, simultaneous pacing in both the ventricle and the atrium can be initiated immediately. Otherwise, one of the techniques depicted in FIG. 2 or 3 can be used for initial delivery of the pacing pulses, with each subsequent pacing cycle being further checked for delivery of the Apace pulse 50 with respect to the "no pacing window" (as exemplified in FIG. 7) to determine if simultaneous pacing can be initiated thereto.

Figure 8:
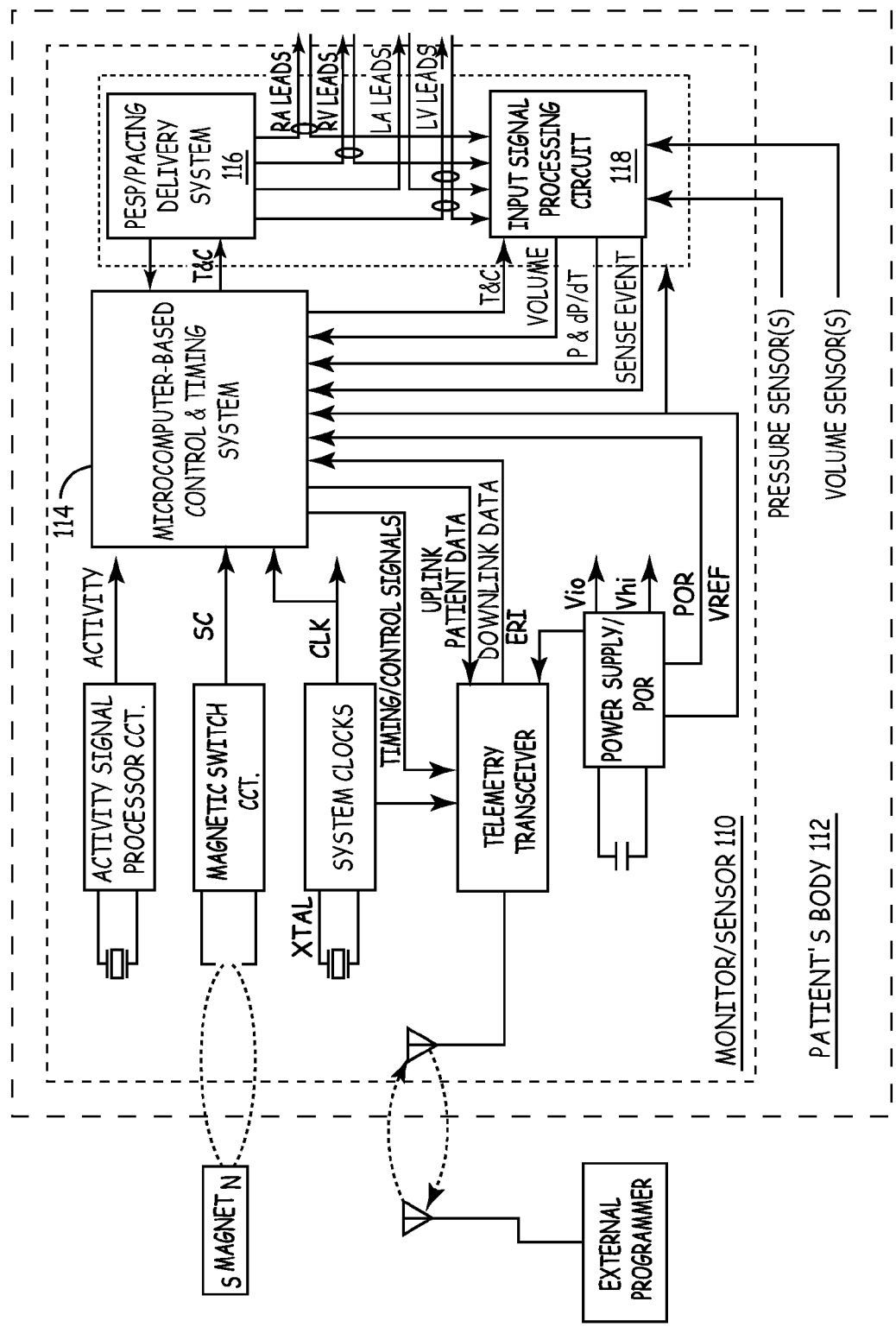
FIG. 8 is a block diagram depicting system architecture from an exemplary multi-chamber monitor/sensor in accordance with certain embodiments of the invention.

FIG. 8 shows a block diagram depicting system architecture of an exemplary multi-chamber monitor/sensor 110 implanted into a patient's body 112 that provides delivery of a therapy and/or physiologic input signal processing. The typical multi-chamber monitor/sensor 110 has a system architecture that is constructed about a microcomputer-based control and timing system 114 which varies in sophistication and complexity depending upon the type and functional features incorporated therein. The functions of microcomputer-based multi-chamber monitor/sensor control and timing system 114 are controlled by firmware and programmed software algorithms stored in RAM and ROM including PROM and EEPROM and are carried out using a CPU or ALU of a typical microprocessor core architecture. The microcomputer-based multi-chamber monitor/sensor control and timing system 114 can also include a watchdog circuit, a DMA controller, a block mover/reader, a CRC calculator, and other specific logic circuitry coupled together by on-chip data bus, address bus, power, clock, and control signal lines in paths or trees in a manner well known in the art. It will also be understood that control and timing of multi-chamber monitor/sensor 110 can be accomplished with dedicated circuit hardware or state machine logic rather than a programmed micro-computer.

The therapy delivery system 116 can be configured to include circuitry for delivering cardioversion/defibrillation shocks and/or cardiac pacing pulses delivered to the heart or cardiomyostimulation to a skeletal muscle wrapped about the heart. Alternately, the therapy delivery system 116 can be configured as a drug pump for delivering drugs into the heart to alleviate heart failure or to operate an implantable heart assist device or pump implanted in patients awaiting a heart transplant operation. The input signal processing circuit 118 includes at least one physiologic sensor signal processing channel for sensing and processing a sensor derived signal from a physiologic sensor located in relation to a heart chamber or elsewhere in the body.

In certain embodiments, the techniques and methods of FIGS. 2-7 are programmed into a controller as part of the microcomputer-based multi-chamber monitor/sensor control and timing system 114; however, the invention should not be limited to such. Instead, it should be appreciated that the controller could be positioned in any number of other manners while still falling within the embodiments of the invention. For example, the controller could be shown separately as its own block wherein it would be connected between the microcomputer-based multi-chamber monitor/sensor control and timing system 114 and the input signal processing circuit 118. In addition, it should be appreciated that certain functionality of the system could be distributed to different components of the multi-chamber monitor/sensor 110 and still fall within the embodiments of the invention. For example, the controller of the invention could have some or all of its functionality incorporated into the mentioned microcomputer-based control and timing system, thereby making the controller expendable.

Figure 9:
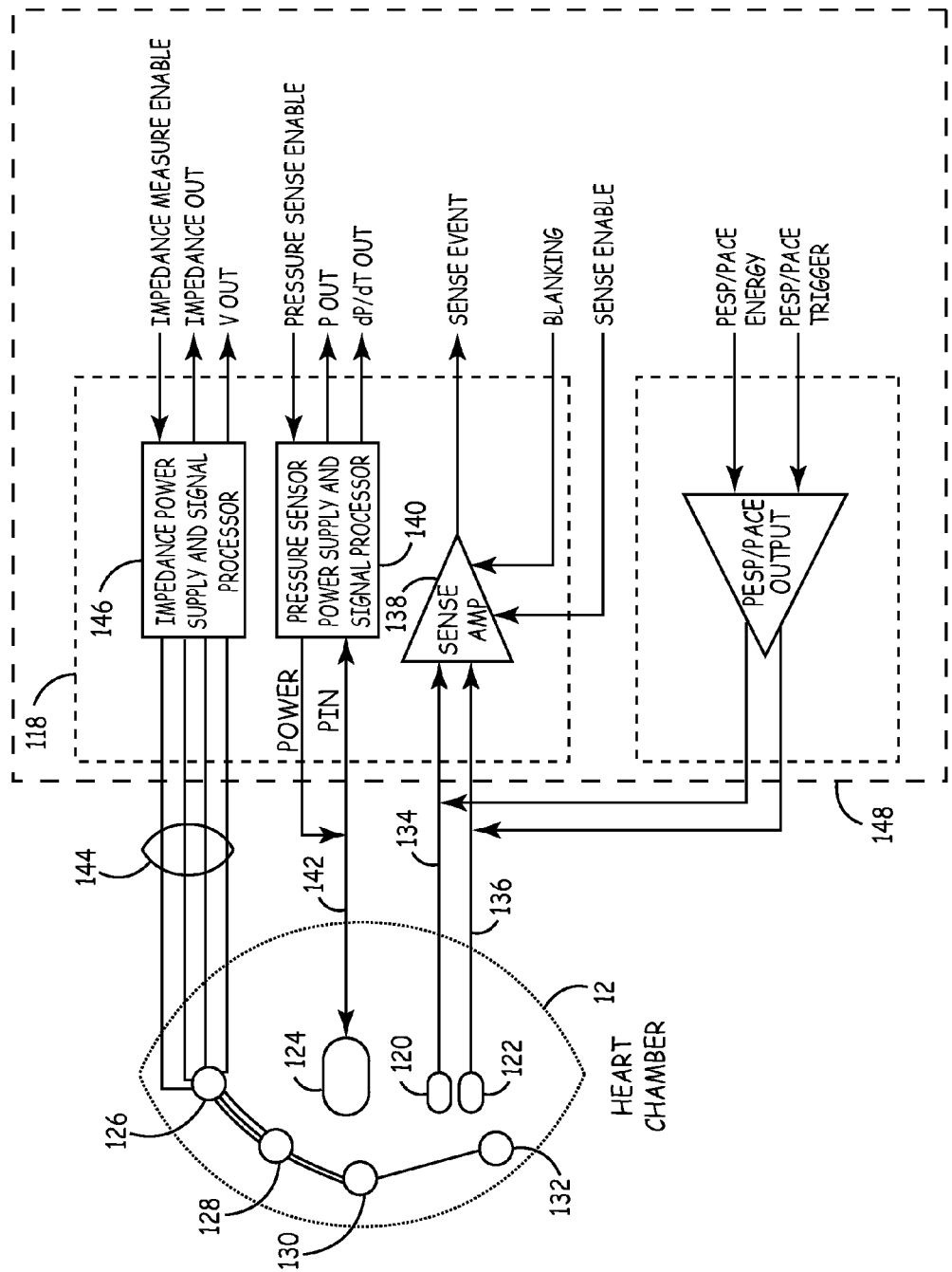
FIG. 9 is a schematic illustration of one pacing, sensing and parameter measuring channel in relation to one heart chamber in accordance with certain embodiments of the invention.

FIG. 9 schematically illustrates one pacing, sensing and parameter measuring channel in relation to one heart chamber. A pair of pace/sense electrodes 120, 122, a pressure sensor 124, and a plurality, e.g., four, impedance measuring electrodes 126, 128, 130, 132 are located in operative relation to the heart 12.

The pair of pace/sense electrodes 120, 122 are located in operative relation to the heart 12 and coupled through lead conductors 134 and 136, respectively, to the inputs of a sense amplifier 138 located within the input signal processing circuit 118. The sense amplifier 138 is selectively enabled by the presence of a sense enable signal that is provided by a control and timing system (not shown, but similar to what is referenced as 114 in FIG. 8). The sense amplifier 138 is enabled during prescribed times when pacing is either enabled or not enabled in a manner known in the pacing art. The blanking signal is provided by the control and timing system upon delivery of a pacing or PESP pulse or pulse train to disconnect the sense amplifier inputs from the lead conductors 134 and 136 for a short blanking period in a manner well known in the art. The sense amplifier provides a sense event signal signifying the contraction of the heart chamber commencing a heart cycle based upon characteristics of the EGM. The control and timing system responds to non-refractory sense events by restarting an escape interval (EI) timer timing out the EI for the heart chamber, in a manner well known in the pacing art.

The pressure sensor 124 is coupled to a pressure sensor power supply and signal processor 140 within the input signal processing circuit 118 through a set of lead conductors 142. The lead conductors 142 convey power to the pressure sensor 124, and convey sampled blood pressure signals from the pressure sensor 124 to the pressure sensor power supply and signal processor 140. The pressure sensor power supply and signal processor 140 samples the blood pressure impinging upon a transducer surface of the sensor 124 located within the heart chamber when enabled by a pressure sense enable signal from the control and timing system. Absolute pressure (P), developed pressure (DP) and pressure rate of change (dP/dt) sample values can be developed by the pressure sensor power supply and signal processor 140 or by the control and timing system for storage and processing.

The set of impedance electrodes 126, 128, 130 and 132 is coupled by a set of conductors 144 and is formed as a lead that is coupled to the impedance power supply and signal processor 146. Impedance-based measurements of cardiac parameters such as stroke volume are known in the art, such as an impedance lead having plural pairs of spaced surface electrodes located within the heart 12. The spaced apart electrodes can also be disposed along impedance leads lodged in cardiac vessels, e.g., the coronary sinus and great vein or attached to the epicardium around the heart chamber. The impedance lead can be combined with the pace/sense and/or pressure sensor bearing lead.

In certain embodiments, the techniques and methods of FIGS. 2-7 are programmed into a controller as part of the control and timing system; however, the invention should not be limited to such. Instead, it should be appreciated that the controller could be positioned in any number of other manners while still falling within the embodiments of the invention. For example, the controller could be shown separately as its own block wherein it would be connected between control and timing system and the input signal processing circuit 118. In addition, it should be appreciated that certain functionality of the system could be distributed to different components of the medical device 148 and still fall within the embodiments of the invention. For example, the controller of the invention could have some or all of its functionality incorporated into the mentioned microcomputer-based control and timing system, thereby making the processor expendable.

It will be appreciated the embodiments of the present invention can take many forms. The true essence and spirit of these embodiments of the invention are defined in the appended claims, and it is not intended the embodiment of the invention presented herein should limit the scope thereof.

What is claimed is:

1. A cardiac medical device for delivering anti-tachycardia pacing, comprising:
   circuitry for delivering cardiac pacing pulses;
   an input signal processing circuit;
   a plurality of electrodes operatively connected to the circuitry and to the input signal processing circuit and implantable within a patient; and
   a controller electrically connected to the circuitry for delivering pacing pulses and to the input signal processing circuit, the controller detecting a tachycardia and controlling the circuitry to deliver a plurality of pacing pulses via the plurality of electrodes in response to detection of the tachycardia via the electrodes, the plurality of pacing pulses including atrial pacing pulses and ventricular pacing pulses, wherein one or more of the atrial pacing pulses is delivered out of phase with a corresponding one or more of the ventricular pacing pulses, and wherein the controller is configured to gradually shift a phase difference between the delivered atrial pacing pulses and the delivered ventricular pacing pulses over a predetermined number of pacing cycles until the pacing pulses are delivered in phase.

2. The cardiac medical device of claim 1, wherein the gradual phase shift includes gradually shifting the timing of the atrial pacing pulses relative to the ventricular pacing pulse.

3. The cardiac medical device of claim 1, wherein the gradual phase shift includes gradually shifting the timing of the ventricular pacing pulses relative to the atrial pacing pulses.

4. The cardiac medical device of claim 1, wherein the gradual phase shift includes maintaining a pacing cycle timing of each ventricular pacing pulse generally constant.

5. The cardiac medical device of claim 1, wherein the controller further delivers generally simultaneous pacing pulses to the atrium and the ventricle over several pacing cycles to provide anti-tachycardia pacing after the pacing pulses are gradually shifted in phase.

6. The cardiac medical device of claim 1, wherein the controller measures a cycle length of the tachycardia, delivers the atrial pacing pulses at a cycle length that is a first predetermined percentage of the tachycardia cycle length, and delivers the ventricular pacing pulses at a cycle length that is a second predetermined percentage of the tachycardia cycle length.

7. The cardiac medical device of claim 6, wherein the first predetermined percentage is greater than the second predetermined percentage.

8. The cardiac medical device of claim 6, wherein the first predetermined percentages and the second predetermined percentage are less than 100 percent.

9. The cardiac medical device of claim 6, wherein the first predetermined percentage and the second predetermined percentage are not equal.

10. The cardiac medical device of claim 1, wherein the controller delivers the atrial pacing pulses at a constant cycle length at least until the atrial and ventricular pacing pulses are delivered in phase.

11. The cardiac medical device of claim 1, wherein the controller delivers the atrial and ventricular pacing pulses at equal cycle lengths after the atrial and ventricular pacing pulses are delivered in phase.

12. The cardiac medical device of claim 1, wherein the controller delivers the pacing pulses together in phase after a determination that simultaneous pacing pulses fall outside vulnerable regions of the cardiac cycle.

13. A computer-readable medium programmed with instructions for delivering anti-tachycardia pacing, the medium comprising instructions for causing a programmable processor to:
   monitor patient parameters in an atrium and a ventricle to detect a tachycardia;
   deliver pacing pulses to the atrium and the ventricle each pacing cycle upon detection of the tachycardia, one or more initial atrial pacing pulses being delivered out of phase with corresponding one or more initial ventricular pacing pulses; and
   gradually shift the phase difference between the pacing pulses delivered in the atrium and the ventricle over a quantity of pacing cycles until the pacing pulses are delivered together in phase each pacing cycle.

14. The computer-readable medium of claim 13, wherein the atrial pacing pulses are delivered at an atrial cycle length and the ventricular pacing pulses are delivered at a ventricular cycle length, and the quantity of pacing cycles of the gradual shift being based on the atrial and ventricular cycle lengths.

15. The computer-readable medium of claim 13, wherein the quantity of pacing cycles of the gradual shift of the phase difference is based on the phase difference of the initial atrial and ventricular pacing pulses.

16. The computer-readable medium of claim 13, wherein the pacing pulses are delivered together in phase after a determination that simultaneous pacing pulses fall outside vulnerable regions of the cardiac cycle.

17. The computer-readable medium of claim 13, wherein the tachycardia comprises one of a supraventricular tachycardia or a ventricular tachyarrhythmia.

18. A method of providing simultaneous atrial and ventricular pacing, comprising:

monitoring patient parameters in an atrium and a ventricle;

detecting an abnormal or suspected abnormal heart rhythm in one of the atrium and the ventricle;

determining whether delivery of simultaneous atrial and ventricular pacing pulses falls within vulnerable regions of the cardiac cycle;

delivering pacing pulses to the atrium and the ventricle each pacing cycle, the atrial pulses being delivered out of phase with the corresponding ventricular pacing pulses if simultaneous delivery of such atrial and corresponding ventricular pacing pulses falls within vulnerable regions of the cardiac cycle;

gradually shifting any out of phase atrial and ventricular pacing pulses relative to each other over a quantity pacing cycles until the pacing pulses are delivered in phase each pacing cycle; and delivering atrial and ventricular pacing pulses in phase.

19. The method of claim 18, wherein the gradual shift of any out of phase pacing pulses comprises one of shifting the atrial pacing pulses relative to the ventricular pacing pulses and shifting the ventricular pacing pulses relative to the atrial pacing pulses.

20. The method of claim 19, further including determining whether to shift the atrial pacing pulse relative to the ventricular pacing pulse or shift the ventricular pacing pulse relative to the atrial pacing pulse, the determination being based on a determination of which shift requires a lesser quantity of pacing cycles to shift the pacing pulses together in phase.

* * * * *